United States Patent [19]
Sakamoto et al.

[11] Patent Number: 5,315,037
[45] Date of Patent: May 24, 1994

[54] PROCESS FOR PURIFICATION OF ACRYLIC ACID

[75] Inventors: Kazuhiko Sakamoto; Hiroaki Tanaka; Masatoshi Ueoka; Yoji Akazawa; Masao Baba, all of Himeji, Japan

[73] Assignee: Nippon Shokubai Co., Ltd., Osaka, Japan

[21] Appl. No.: 222

[22] Filed: Jan. 4, 1993

[30] Foreign Application Priority Data

Jan. 9, 1992 [JP] Japan .................................. 4-002331

[51] Int. Cl.⁵ ...................... C07C 51/16; C07C 51/42
[52] U.S. Cl. ...................................... 562/545; 562/600
[58] Field of Search ............................... 562/545, 600

[56] References Cited

U.S. PATENT DOCUMENTS 3,859,175   1/1975   Ohrui et al. ......................... 562/600
4,147,721   4/1979   Leacock ............................. 562/532

FOREIGN PATENT DOCUMENTS 1120284   7/1968   United Kingdom .
1427223   3/1976   United Kingdom .

*Primary Examiner*—José G. Dees
*Assistant Examiner*—Joseph M. Conrad, III
*Attorney, Agent, or Firm*—Oblon, Spivak, McClelland, Maier & Neustadt

[57] ABSTRACT

A process for producing acrylic acid is described, which process comprising providing a mixed gas of acrylic acid and by-products produced by catalytic gas phase oxidation of propylene and/or acrolein, contacting the mixed gas with water to obtain an aqueous solution, and adding an azeotrope solvent to the aqueous solution for distillation to obtain a mixture of the by-products, water and the azeotrope solvent from a tower top and acrylic acid from a tower bottom. Highly pure acrylic acid is obtained by using, as the azeotrope solvent, a mixed solvent of solvent A selected from diethyl ketone, methyl propyl ketone, methyl isobutyl ketone, methyl-tert-butyl ketone, n-propyl acetate and mixtures thereof and solvent B selected from toluene, heptane, methyl cyclohexane and mixtures thereof.

24 Claims, 1 Drawing Sheet

PROCESS FOR PURIFICATION OF ACRYLIC ACID

BACKGROUND OF THE INVENTION

1. Field of the Invention

This invention generally relates to a process for producing acrylic acid by catalytic gas phase oxidation of propylene and/or acrolein (which may be sometimes referred simply to as propylene etc.) with molecular oxygen-containing gas. The invention particularly relates to a process for producing highly pure acrylic acid by efficiently separating by-products, particularly acetic acid, from the reaction product obtained by the catalytic gas phase oxidation. More particularly, the invention relates to a process for producing highly pure acrylic acid wherein water is added to the reaction product to obtain an aqueous solution of the product to which an azeotrope solvent is further added thereby removing by-products through the azeotropic phenomenon.

2. Description of the Related Art

The catalytic gas phase oxidation of propylene etc., with molecular oxygen-containing gas in the presence of a catalyst for oxidation provides a reaction product in the form of a mixed gas which contains, aside from intended acrylic acid, by-products such as acetic acid, formic acid, acetaldehyde, formaldehyde and the like and unreacted starting materials such as propylene, acrolein and the like. In known processes of industrially producing acrylic acid by catalytic gas phase oxidation of propylene etc., with molecular oxygen-containing gas. the mixed gas obtained by the catalytic gas phase oxidation is introduced into an acrylic gas absorption tower. In the tower, the gas is contacted with water for cooling and absorption, thereby obtaining an aqueous solution containing acrylic acid and the by-products such as acetic acid. Then, acrylic acid is separated and purified from the aqueous solution by distillation.

Among the by-products, acetic acid is undesirably produced in comparatively large amounts. Since acetic acid has a high distillation temperature (boiling point of 118.1° C. under atomic pressures), the separation by distillation involves the problem that acrylic acid is liable to polymerize during the distillation and that the relative volatility between acrylic acid and acetic acid is so close that it is difficult to simply separate one from another by distillation. To avoid this, there has been carried out a process wherein an azeotropic phenomenon of a three-component system consisting of acetic acid-water-azeotrope solvent or a multi-component system is utilized. More particularly, the reaction product is contacted with water to obtain an aqueous solution, to which an azeotrope solvent is added, followed by distillation to distil off a mixture of acetic acid-water-azeotrope solvent from the top of a distillator and to collect acrylic acid from the tower bottom.

In Japanese Patent Publication No. sho 63-10691, toluene is employed as the azeotrope solvent. Although most of the acetic acid could be azeotropically separated, part of the acid would be left unseparated, resulting in the discharge from the bottom of an azeotropic separation tower along with acrylic acid. This leads to further separation of the unseparated acetic acid by use of an acetic acid separation tower, thus needing two towers including the azeotropic separation tower and the acetic acid separation tower.

In Japanese Patent Publication Nos. sho 46-34691 and 46-18967, azeotropic distillation is performed using ethyl acetate, butyl acetate, dibutyl ether, ethyl acetate, hexane, heptane, ethyl methacrylate, propyl acrylate and the like. The azeotrope solvent, acetic acid and water are distilled off from the top of the tower and acrylic acid is obtained from the bottom of the tower. However, our investigations have revealed that mere removal of high boiling points' impurities through distillation of acrylic acid obtained from the tower bottom according to these processes is not satisfactory with respect to the removal of acetic acid, such acrylic acid being unsatisfactory for use as an acrylic acid product.

It will be noted that the impurities other than acetic acid mentioned as contained in the by-products, e.g. formic acid (boiling point: 100.8° C.), acetaldehyde (boiling point: 20.8° C.), formaldehyde (boiling point: $-19.5°$ C.) and acrolein (boiling point: 52.5° C.), are all low in boiling point and can be readily removed without resorting to the azeotropic treatment.

SUMMARY OF THE INVENTION

An object of the invention is to solve the above prior art problems and to provide a process for producing highly pure acrylic acid wherein a mixed gas obtained by catalytic gas phase oxidation of propylene and/or acrolein is contacted with water to obtain an acrylic acid aqueous solution comprising acrylic acid and by-products such as acetic acid, to which a selected azeotrope solvent is added and the resulting mixture is subjected to azeotropic distillation to distil off the azeotrope solvent, acetic acid and water from the top of a distillator and to obtain acrylic acid from a bottom of the distillator such that substantially all of the azeotrope solvent, acetic acid and water are distilled off from the top of a distillator and substantially only acrylic acid is withdrawn from a bottom of the distillator.

Another object of the invention is to provide a process for producing highly pure acrylic acid wherein the liquid withdrawn from the bottom can be used, as it is, as a starting material for preparing acrylic esters and when the liquid is subjected to further distillation to remove high boiling impurities therefrom, there is obtained an acrylic acid product of high quality.

A further object of the invention is to provide a process for producing highly pure acrylic acid wherein an mixed solvent of two or more azeotrope solvents in combination at defined mixing ratio is provided as an azeotrope solvent for carrying out optimum distillation.

Another object of the invention is to provide a process for producing highly pure acrylic acid in an industrially beneficial manner wherein a mixture of acetic acid-water-azeotrope solvent obtained from the top of an azeotropic separator is separated, and water is used to provide the acrylic acid aqueous solution and an azeotrope solvent is used for recycling in the production system.

Other objects and features of the invention will be understood from the description which follows, along with the advantages which will be readily understood to those skilled in the art.

DETAILED DESCRIPTION OF THE INVENTION

Figure 1:
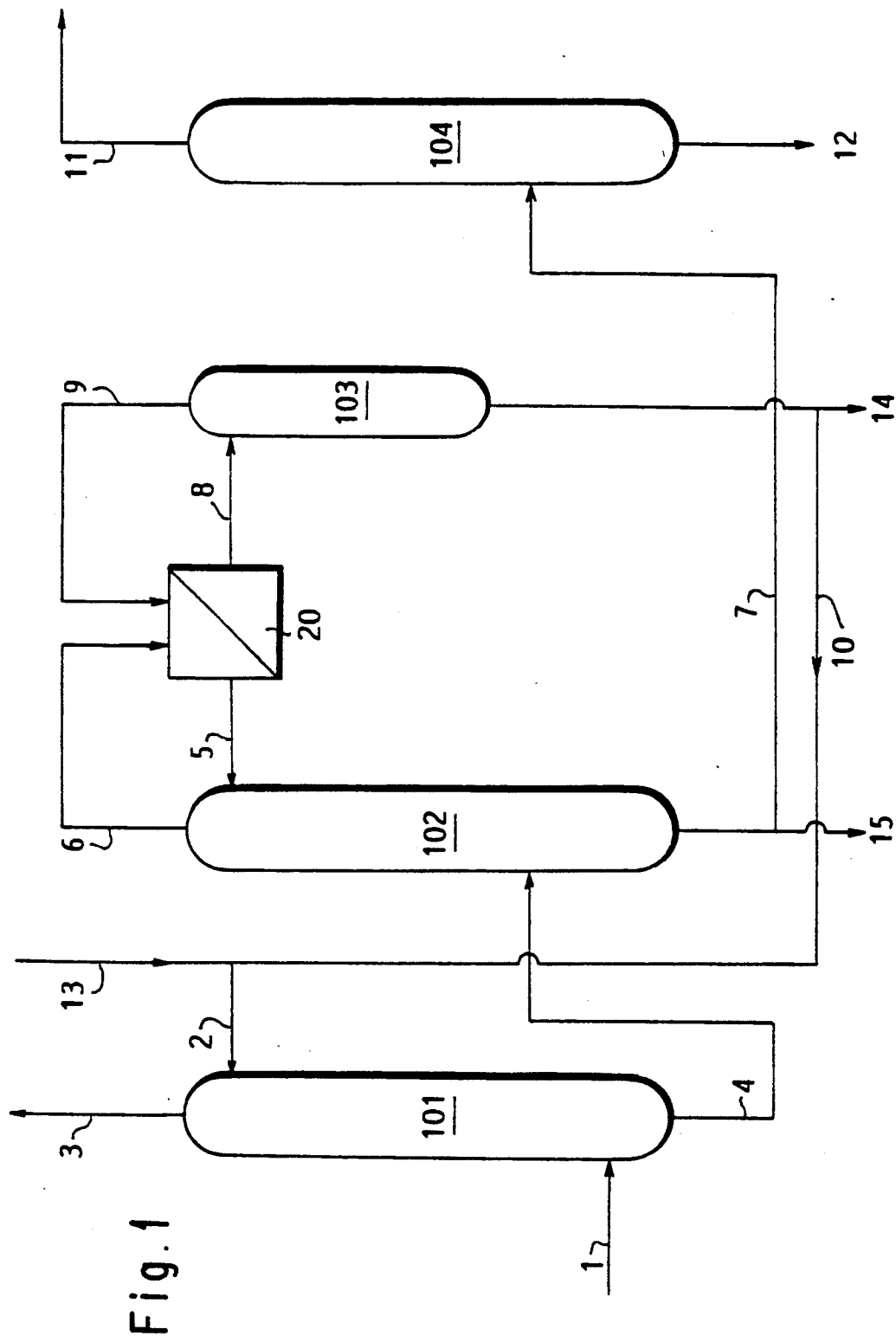
FIG. 1 is a flow chart showing a process according to the invention.

An important technical concept or feature of the invention for achieving the above objects resides in the use of a mixed solvent of the following solvents A and B as an azeotrope solvent.

Solvent A: at least one solvent selected from the group consisting of diethyl ketone, methyl propyl ketone, methyl isobutyl ketone, methyl-tert-butyl ketone and n-propyl acetate.

Solvent B: at least one solvent selected from the group consisting of toluene, heptane and methylcyclohexane.

The above technical concept can be realized by embodiments according to the invention. A typical embodiment of the invention is described with reference to FIG. 1 and by way of examples, which should not be construed as limiting the invention thereto.

Reference is now made to FIG. 1.

In FIG. 1, a mixed gas which is obtained by catalytic gas phase oxidation of propylene and/or acrolein with a molecular oxygen-containing gas is introduced from line 1 into an acrylic acid absorption tower 101 wherein the gas is contacted with water passed from line 2, thereby obtaining an acrylic acid aqueous solution, which contains acrylic acid and by-products such as acetic acid and the like, from line 4. Water which is fed to the acrylic acid absorption tower 101 from line 2 may be one which is fed freshly from line 13. As will be described hereinafter, it is preferred to use, as the said water, an acetic acid aqueous solution discharged from the bottom of a solvent stripping tower 103.

With the flow chart of FIG. 1, the acrylic acid aqueous solution which is discharged from the bottom of the acrylic acid absorption tower 101 through line 4 may be directly fed without any treatment, to an azeotropic separation tower 102. The acrylic acid aqueous solution from line 4, however, is fed to the acrolein stripping tower which is optionally provided (not shown in FIG. 1) wherein acrolein dissolved in the acrylic acid aqueous solution is caused to strip in this tower, and thereafter, the resultant acrylic acid aqueous solution is fed to the azeotropic separation tower 102. In this case, the stripped acrolein should be collected and recycled to the reaction system.

In the azeotropic separation tower 102, the acrylic acid aqueous solution and an azeotrope solvent which are respectively fed from lines 4 and 5 are subjected to azeotropic distillation. By this, the azeotrope solvent, acetic acid and water are distilled off from the top of the tower 102 and acrylic acid is obtained from the tower bottom.

In the practice of the invention, although depending on the amount of water through line 2 fed to the acrylic acid absorption tower 101 and other operating conditions, the acrylic acid aqueous solution in the azeotropic tower 102 generally contain, under ordinary conditions of preparing acrylic acid, 50 to 80 wt% of acrylic acid, 2 to 5 wt% of acetic acid and the balance being water The azeotrope solvent used in the invention is a mixed solvent of the afore-indicated Solvents A and B.

The kind of Solvent A and Solvent B are those which have been set out before and all the combinations of these two types of solvents produce good results. Choice of Solvents A and B in combination is left to one who carries out the process of the invention. Compounds of Solvent A are all hydrophilic in nature. Of the compounds of Solvent A, methyl iso-butyl ketone is most preferred when taking into consideration the azeotropic composition with water, the azeotropic temperature and the costs as a whole. Compounds of Solvent B are high in affinity for acetic acid and are expected to form an azeotrope with acetic acid. Depending on the progress of the reaction, an optimum solvent should be selected.

By the use of a specific type of mixed solvent as an azeotrope solvent, a mixture which consists essentially of acetic acid, water and the azeotrope solvent is distilled off from the top of the azeotropic separation tower 102. Moreover, acrylic acid which is substantially free of acetic acid, water and the azeotrope solvent is obtained from the bottom. The mixing ratio between Solvents A and B fed from line 5 is preferably in the range of 50:50 to 75:25 on the weight basis. If the Solvent A exceeds the above range, the concentration of acetic acid at the tower bottom becomes too high. On the contrary, when Solvent B is used in larger amounts, the amount of acrylic acid distilled from the tower top is undesirably increased.

The mixture consisting substantially of acetic acid, water and the azeotrope solvent which has been distilled off from the top of the azeotrope separation tower 102 is received in a reservoir 20. In the reservoir 20, the mixture is separated into an organic phase comprised mainly of the azeotrope solvent and an aqueous phase comprised mainly of acetic acid and water. The organic phase is circulated through line 5 to the azeotropic separation tower 102. On the other hand, the aqueous phase is passed through line 8 into the solvent stripping tower 103 for distillation. As a consequence, the azeotrope solvent is distilled off from the top of the solvent stripping tower 103 and returned through line 9 to the reservoir 20. An acetic acid aqueous solution consisting substantially of acetic acid and water i withdrawn through line 14 from the bottom of the solvent stripping tower 103 and discharged to outside. Of course, the acetic acid aqueous solution may be recycled through line 10 to the acrylic acid absorption tower 101 for us as water which is contacted with the mixed gas obtained by the catalytic gas phase oxidation. By this, the acetic acid aqueous solution is not only merely recovered and recycled, but also used as water for contact with the mixed gas obtained by the catalytic gas phase oxidation. This leads to the advantage that the use of acetic acid aqueous solution for contact with the mixed gas is higher in the acrylic acid-absorption efficiency that water alone, resulting in a reduced number of absorption stages required in the acrylic acid absorption tower 101. This is considered for the reason that acetic acid in the acetic acid aqueous solution has good affinity for acrylic acid. In order not to increase the concentration of acetic acid during the course of recycling through the reaction system, it is convenient to control the feed of water from line 13 and the amount of the acetic acid aqueous solution withdrawn from line 14 thereby keeping the total balance in the system.

The acrylic acid withdrawn from the bottom of the azeotropic separation tower 102 may be fed through line 15 to an esterification process, by which the acid can be used, as it is, as a starting material for preparing acrylic esters. For obtaining a highly pure acrylic acid product, the acrylic acid is introduced through line 7 into a high boiling separation tower 104 wherein it is distilled to withdraw high boiling points' materials such as polymers from the bottom through line 12. The acrylic acid product is obtained from the tower top through line 11.

Since a specific type of mixed azeotrope solvent is used in the practice of the invention, little acrylic acid is distilled off from the top of the azeotropic separation tower. In addition, there is obtained from the tower bottom acrylic acid which is substantially free of acetic acid, water and the azeotropic solvent. The bottom liquid from the azeotropic separation tower may be used, as it is, as a starting material for preparing acrylic esters. If this acid is distilled in a high boiling separation tower, an acrylic acid product with a higher purity can be achieved. In prior art, it is usual that an acetic acid separation tower is provided downstream of the azeotropic separation tower to separate remaining acetic acid. In the practice of the present invention, this acetic acid separation tower becomes unnecessary, thus simplifying the process of producing acrylic acid.

The invention is more particularly described by way of examples.

EXAMPLE 1

A mixed gas which was obtained by catalytic gas phase oxidation of propylene with a molecular oxygen-containing gas was introduced into an acrylic acid absorption tower for contacting with water to obtain an aqueous solution. This solution was passed into an acrolein stripping tower wherein acrolein was stripped, thereby obtaining an acrylic acid aqueous solution containing 30 wt% of water and 3.0 wt% of acetic acid. This acrylic acid aqueous solution was subjected to azeotropic distillation by the use of an azeotropic separation tower 102 which had a sieve tray with 60 stages and a stage distance of 147 mm and which was equipped with a distillation line at the top thereof, a starting material feed line at the central portion, and a bottom liquid withdrawing line at the bottom. In this case, a mixed solvent of methyl isobutyl ketone and toluene (at a mixing ratio by weight of 65:35) was used as an azeotrope solvent.

The stationary running conditions included a tower top temperature of 47° C. of the azeotropic separation tower 102, a tower bottom temperature of 98° C., a tower top pressure of 100 mmHg, a refluxing ratio (the total moles of a refluxing solution per unit time/the total moles of a distillate per unit time) of 1.42, and a starting material feed of 7.59 liter/hour from line 4. The aqueous phase from line 8 contained 6.7 wt% of acetic acid and 0.5 wt% of acrylic acid, whereas the liquid withdrawn from the bottom of the azeotropic separation tower through line 15 contained 97.0 wt% of acrylic acid, 0.03 wt% of acetic acid, 0.001 wt% of the solvent and 2.97 wt% of the others.

The aqueous phase from line 8 was fed to the solvent stripping tower 103 and the solvent was recovered from the top of the tower through line 9, whereas acetic acid aqueous solution withdrawn from the bottom of the tower through line 10 contained 7.1 wt% of acetic acid, 0.53 wt% of acrylic acid, which was recycled to the acrylic acid absorption tower 101 and used for absorbent to contact with the mixed gas by catalytic gas phase oxidation.

COMPARATIVE EXAMPLE 1

The general procedure of Example 1 was repeated excepting that methyl isobutyl ketone was used as the azeotrope solvent and the refluxing ratio was 1.43, thereby carrying out the azeotropic distillation of the acrylic acid aqueous solution.

At the stationary run, the aqueous phase of line 8 contained 6.6 wt% of acetic acid and 4.0 wt% of acrylic acid which was about 8 times that of Example 1. On the other hand, the liquid withdrawn from the bottom of the azeotropic separation tower 102 through line 15 contained 96.9 wt% of acrylic acid, 0.2 wt% of acetic acid, 0.01 wt% of the solvent and 2.92 wt% of the others. Thus, the amount of acetic acid was higher by one order of magnitude than in Example 1.

COMPARATIVE EXAMPLE 2

The general procedure of Example 1 was repeated excepting that toluene was used as the azeotrope solvent and the refluxing ratio was 1.23, thereby carrying out the azeotropic distillation of the acrylic acid aqueous solution.

At the stationary run, the aqueous phase of line 8 contained 6.7 wt% of acetic acid and 5.8 wt% of acrylic acid which was about 10 times that of Example 1. On the other hand, the liquid withdrawn from the bottom of the azeotropic separation tower 102 through line 15 contained 97.0 wt% of acrylic acid, 0.03 wt% of acetic acid, 0.01 wt% of the solvent and 2.96 wt% of the others.

EXAMPLE 2

The general procedure of Example 1 was repeated excepting that a mixed solvent of methyl isobutyl ketone and heptane (mixing ratio by weight of 65:35) was used as the azeotrope solvent and the refluxing ratio was 1.65, thereby carrying out the azeotropic distillation of the acrylic acid aqueous solution.

At the stationary run, the aqueous phase of line 8 contained 6.6 wt% of acetic acid and 0.6 wt% of acrylic acid. On the other hand, the liquid withdrawn from the bottom of the azeotropic separation tower 102 through line 15 contained 96.9 wt% of acrylic acid, 0.03 wt% of acetic acid, 0.01 wt% of the solvent and 3.07 wt% of the others.

EXAMPLE 3

The general procedure of Example 1 was repeated excepting that a mixed solvent of methyl-tert-butyl ketone and toluene (mixing ratio by weight of 65:35) was used as the azeotrope solvent and the refluxing ratio was 1.89, thereby carrying Out the azeotropic distillation of the acrylic acid aqueous solution.

At the stationary run, the aqueous phase of line 8 contained 6.7 wt% of acetic acid and 0.5 wt% of acrylic acid. On the other hand, the liquid withdrawn from the bottom of the azeotropic separation tower 102 through line 15 contained 97.3 wt% of acrylic acid, 0.03 wt% of acetic acid, 0.001 wt% of the solvent and 2.67 wt% of the others.

EXAMPLE 4

The general procedure of Example 1 was repeated excepting that a mixed solvent of methyl-tert-butyl ketone and heptane (mixing ratio by weight of 65:35) was used as the azeotrope solvent and the refluxing ratio was 1.99, thereby carrying out the azeotropic distillation of the acrylic acid aqueous solution.

At the stationary run, the aqueous phase of line 8 contained 6.6 wt% of acetic acid and 0.5 wt% of acrylic acid. On the other hand, the liquid withdrawn from the bottom of the azeotropic separation tower 102 through line 15 contained 97.2 wt% of acrylic acid, 0.03 wt% of acetic acid, 0.001 wt% of the solvent and 2.77 wt% of the others.

COMPARATIVE EXAMPLE 3

The general procedure of Examples 1 was repeated excepting that the mixing ratio by weight of methyl isobutyl ketone and toluene was 85:15 and the refluxing ratio was 1.41, thereby carrying out the azeotropic distillation of the acrylic acid aqueous solution.

At the stationary run, the aqueous phase of line 8 contained 5.8 wt% of acetic acid and 0.5 wt% of acrylic acid. On the other hand, the liquid withdrawn from the bottom of the azeotropic separation tower 102 through line 15 contained 97.3 wt% of acrylic acid, 0.10 wt% of acetic acid, 0.01 wt% of the solvent and 2.59 wt% of the others.

EXAMPLE 5

The general procedure of Example 1 was repeated excepting that the mixing ratio by weight of methyl isobutyl ketone and toluene was 50:50 and the refluxing ratio was 1.49, thereby carrying out the azeotropic distillation of the acrylic acid aqueous solution.

At the stationary run, the aqueous phase of line 8 contained 6.7 wt% of acetic acid and 0.5 wt% of acrylic acid. On the other hand, the liquid withdrawn from the bottom of the azeotropic separation tower 102 through line 15 contained 96.8 wt% of acrylic acid, 0.03 wt% of acetic acid, 0.001 wt% of the solvent and 3.17 wt% of the others.

EXAMPLE 6

The general procedure of Example 1 was repeated excepting that a mixed solvent of methyl isobutyl ketone and methylcyclohexane (mixing ratio by weight of 65:35) was used as the azeotrope solvent and the refluxing ratio was 1.25, thereby carrying out the azeotropic distillation of the acrylic acid aqueous solution.

At the stationary run, the aqueous phase of line 8 contained 6.6 wt% of acetic acid and 0.5 wt% of acrylic acid. On the other hand, the liquid withdrawn from the bottom of the azeotropic separation tower 102 through line 15 contained 97.3 wt% of acrylic acid, 0.03 wt% of acetic acid, 0.001 wt% of the solvent and 2.67 wt% of the others.

EXAMPLE 7

The general procedure of Example 1 was repeated excepting that a mixed solvent of methyl-tert-butyl ketone and methylcyclohexane (mixing ratio by weight of 65:35) was used as the azeotrope solvent and the refluxing ratio was 1.60, thereby carrying out the azeotropic distillation of the acrylic acid aqueous solution.

At the stationary run, the aqueous phase of line 8 contained 6.8 wt% of acetic acid and 0.5 wt% of acrylic acid. On the other hand, the liquid withdrawn from the bottom of the azeotropic separation tower 102 through line 15 contained 97.4 wt% of acrylic acid, 0.03 wt% of acetic acid, 0.001 wt% of the solvent and 2.57 wt% of the others.

EXAMPLE 8

The general procedure of Example 1 was repeated excepting that a mixed solvent of diethyl ketone and toluene (mixing ratio by weight of 65:35) was used as the azeotrope solvent and the refluxing ratio was 1.58, thereby carrying out the azeotropic distillation of the acrylic acid aqueous solution.

At the stationary run, the aqueous phase of line 8 contained 6.2 wt% of acetic acid and 0.5 wt% of acrylic acid. On the other hand, the liquid withdrawn from the bottom of the azeotropic separation tower 102 through line 15 contained 97.2 wt% of acrylic acid, 0.03 wt% of acetic acid, 0.001 wt% of the solvent and 2.77 wt% of the others..

EXAMPLE 9

The general procedure of Example 1 was repeated excepting that a mixed solvent of diethyl ketone and heptane (mixing ratio by weight of 65:35) was used as the azeotrope solvent and the refluxing ratio was 1.83, thereby carrying out the azeotropic distillation of the acrylic acid aqueous solution.

At the stationary run, the aqueous phase of line 8 contained 6.0 wt% of acetic acid and 0.4 wt% of acrylic acid. On the other hand, the liquid withdrawn from the bottom of the azeotropic separation tower 102 through line 15 contained 97.0 wt% of acrylic acid, 0.03 wt% of acetic acid, 0.001 wt% of the solvent and 2.97 wt% of the others.

EXAMPLE 10

The general procedure of Example 1 was repeated excepting that a mixed solvent of diethyl ketone and methylcyclohexane (mixing ratio by weight of 65:35) was used as the azeotrope solvent and the refluxing ratio was 1.34, thereby carrying out the azeotropic distillation of the acrylic acid aqueous solution.

At the stationary run, the aqueous phase of line 8 contained 6.1 wt% of acetic acid and 0.4 wt% of acrylic acid. On the other hand, the liquid withdrawn from the bottom of the azeotropic separation tower 102 through line 15 contained 97.4 wt% of acrylic acid, 0.03 wt% of acetic acid, 0.001 wt% of the solvent and 2.57 wt% of the others.

EXAMPLE 11

The general procedure of Example 1 was repeated excepting that a mixed solvent of methyl propyl ketone and toluene (mixing ratio by weight of 65:35) was used as the azeotrope solvent and the refluxing ratio was 1.67, thereby carrying out the azeotropic distillation of the acrylic acid aqueous solution.

At the stationary run, the aqueous phase of line 8 contained 6.1 wt% of acetic acid and 0.4 wt% of acrylic acid. On the other hand, the liquid withdrawn from the bottom of the azeotropic separation tower 102 through line 15 contained 97.3 wt% of acrylic acid, 0.03 wt% of acetic acid, 0.001 wt% of the solvent and 2.67 wt% of the others.

EXAMPLE 12

The general procedure of Example 1 was repeated excepting that a mixed solvent of methyl propyl ketone and heptane (mixing ratio by weight of 65:35) was used as the azeotrope solvent and the refluxing ratio was 1.94, thereby carrying out the azeotropic distillation of the acrylic acid aqueous solution.

At the stationary run, the aqueous phase of line 8 contained 6.0 wt% of acetic acid and 0.4 wt% of acrylic acid. On the other hand, the liquid withdrawn from the bottom of the azeotropic separation tower 102 through line 15 contained 97.1 wt% of acrylic acid, 0.03 wt% of acetic acid, 0.001 wt% of the solvent and 2.87 wt% of the others.

EXAMPLE 13

The general procedure of Example 1 was repeated excepting that a mixed solvent of methyl propyl ketone and methylcyclohexane (mixing ratio by weight of 65:35) was used as the azeotrope solvent and the refluxing ratio was 1.58, thereby carrying out the azeotropic distillation of the acrylic acid aqueous solution.

At the stationary run, the aqueous phase of line 8 contained 6.2 wt% of acetic acid and 0.5 wt% of acrylic acid. On the other hand, the liquid withdrawn from the bottom of the azeotropic separation tower 102 through line 15 contained 97.1 wt% of acrylic acid, 0.03 wt% of acetic acid, 0.001 wt% of the solvent and 2.87 wt% of the others.

EXAMPLE 14

The general procedure of Example 1 was repeated excepting that a mixed solvent of n-propyl acetate and toluene (mixing ratio by weight of 65:35) was used as the azeotrope solvent and the refluxing ratio was 2.10, thereby carrying out the azeotropic distillation of the acrylic acid aqueous solution.

At the stationary run, the aqueous phase of line 8 contained 6.2 wt% of acetic acid and 0.5 wt% of acrylic acid. On the other hand, the liquid withdrawn from the bottom of the azeotropic separation tower 102 through line 15 contained 97.5 wt% of acrylic acid, 0.03 wt% of acetic acid, 0.001 wt% of the solvent and 2.47 wt% of the others.

EXAMPLE 15

The general procedure of Example 1 was repeated excepting that a mixed solvent of n-propyl acetate and toluene (mixing ratio by weight of 65:35) was used as the azeotrope solvent and the refluxing ratio was 2.14, thereby carrying out the azeotropic distillation of the acrylic acid aqueous solution.

At the stationary run, the aqueous phase of line 8 contained 6.2 wt% of acetic acid and 0.5 wt% of acrylic acid. On the other hand, the liquid withdrawn from the bottom of the azeotropic separation tower 102 through line 15 contained 97.4 wt% of acrylic acid, 0.03 wt% of acetic acid, 0.001 wt% of the solvent and 2.57 wt% of the others.

EXAMPLE 16

The general procedure of Example 1 was repeated excepting that a mixed solvent of n-propyl acetate and methylcyclohexane (mixing ratio by weight of 65:35) was used as the azeotrope solvent and the refluxing ratio was 1.66, thereby carrying out the azeotropic distillation of the acrylic acid aqueous solution.

At the stationary run, the aqueous phase of line 8 contained 6.3 wt% of acetic acid and 0.5 wt% of acrylic acid. On the other hand, the liquid withdrawn from the bottom of the azeotropic separation tower 102 through line 15 contained 97.3 wt% of acrylic acid, 0.03 wt% of acetic acid, 0.001 wt% of the solvent and 2.67 wt% of the others.

It should be noted that various variations and modifications of the invention can be made to the embodiments and examples set out hereinbefore without departing from the spirit and scope of the invention as defined in the following claims.

What we claim is:

1. In a process for producing acrylic acid in which propylene, acrolein or a mixture thereof are subjected to catalytic gas phase oxidation with a molecular oxygen-containing gas to obtain a mixed gas, contacting the mixed gas with water in an acrylic acid absorption tower to obtain an acrylic acid aqueous solution, and introducing the acrylic acid aqueous solution into an azeotropic separation tower for distillation of the acrylic acid aqueous solution along with the azeotrope solvent to separate acrylic acid from the acrylic acid aqueous solution, the improvement wherein said azeotrope solvent is a mixed solvent consisting of at least one solvent A selected from the group consisting of diethyl ketone, methyl propyl ketone, methyl isobutyl ketone, methyl-tert-butyl ketone and n-propyl acetate and at least one solvent B selected from the group consisting of toluene, heptane and methylcyclohexane whereby a mixture consisting substantially of acetic acid, water and the azeotrope solvent is distilled off from the top of the azeotropic separation tower and acrylic acid which is substantially free of acetic acid, water and the azeotrope solvent is obtained from the bottom of the tower.

2. A process according to claim 1, wherein the mixing ratio by weight between the solvent A and the solvent B in the azeotrope solvent is in the range of 50:50 to 75:25.

3. A process according to claim 1 or 2, wherein the acrylic acid aqueous solution introduced into the azeotropic separation tower comprises 50 to 80 wt% of acrylic acid, 2 to 5 wt% of acetic acid and 20 to 40 wt% of water.

4. A process according to any of claims 1 to 3, wherein the mixture consisting substantially of acetic acid, water and the azeotrope solvent obtained from the top of the azeotropic separation tower is introduced into a solvent stripping tower and distilled to obtain a distillate containing the azeotrope solvent from the top of the solvent stripping tower and also to obtain an acetic acid aqueous solution consisting substantially of acetic acid and water from the bottom of the solvent stripping tower, said distillate being recycled to the azeotropic separation tower, said acetic aqueous solution being recycled to the acrylic acid absorption tower for contacting with the mixed gas obtained by the catalytic gas phase oxidation.

5. A process according to claim 1, wherein solvent B is toluene.

6. A process of claim 1, wherein solvent B is heptane.

7. A process of claim 1, wherein solvent B is methylcyclohexane.

8. A process of claim 5, wherein said azeotrope solvent is a mixture of methyl isobutyl ketone and toluene.

9. A process of claim 6, wherein said azeotrope solvent is a mixture of methyl isobutyl ketone and heptane.

10. A process of claim 5, wherein said azeotrope solvent is a mixture of methyl-tert-butyl ketone and toluene.

11. A process of claim 6, wherein said azeotrope solvent is a mixture of methyl-tert-butyl ketone and heptane.

12. A process of claim 7, wherein said azeotrope solvent is a mixture of methyl isobutyl ketone and methylcyclohexane.

13. A process of claim 7, wherein said azeotrope solvent is a mixture of methyl-tert-butyl ketone and methylcyclohexane.

14. A process of claim 5, wherein said azeotrope solvent is a mixture of diethylketone and toluene.

15. A process of claim 6, wherein said azeotrope solvent is a mixture of diethyl ketone and heptane.

16. A process of claim 7, wherein said azeotrope solvent is a mixture of diethyl ketone and methylcyclohexane.

17. A process of claim 5, wherein said azeotrope solvent is a mixture of methyl propyl ketone and toluene.

18. A process of claim 6, wherein said azeotrope solvent is a mixture of methyl propyl ketone and heptane.

19. A process of claim 7, wherein said azeotrope solvent is a mixture of methyl propyl ketone and methylcyclohexane.

20. A process of claim 5, wherein said azeotrope solvent is a mixture of n-propyl acetate and toluene.

21. A process of claim 7, wherein said azeotrope solvent is a mixture of n-propyl acetate and methylcyclohexane.

22. A process for obtaining acrylic acid from an aqueous acrylic acid solution containing acrylic, acetic acid and water, comprising the steps of:

charging said aqueous acrylic acid solution into a single azeotropic distillation column;

adding an azeotrope solvent to the top of said azeotropic distillation column, wherein said azeotrope solvent is a mixed solvent consisting of at least one solvent A selected from the group consisting of diethyl ketone, methyl propyl ketone, methyl isobutyl ketone, methyl-tert-butyl ketone and n-propyl acetate and at least one solvent B selected from the group consisting of toluene, heptane and methylcyclohexane, wherein the weight ratio of A:B is 50:50 to 75:25;

azeotropically distilling said aqueous acrylic acid solution and said azeotrope solvent; and withdrawing an acrylic acid-containing product stream from the bottom of said azeotropic distillation column.

23. A process according to claim 22, wherein said product stream contains at least 96.8 wt.% acrylic acid.

24. A process according to claim 22, wherein said product stream contains 0.03 wt.% or less acetic acid.

* * * * *